United States Patent [19]

Wiedemann et al.

[11] 4,029,783
[45] June 14, 1977

[54] N-SUBSTITUTED 1-AMINO-3-PHENOXY-PROPAN-2-OL COMPOUNDS AND THERAPEUTIC COMPOSITIONS CONTAINING THEM

[75] Inventors: Fritz Wiedemann; Max Thiel, both of Mannheim; Kurt Stach, Mannheim-Waldhof; Karl Dietmann, Mannheim-Vogelstang; Gisbert Sponer, Hemsbach, all of Germany

[73] Assignee: Boehringer Mannheim G.m.b.H., Mannheim-Waldhof, Germany

[22] Filed: Dec. 8, 1975

[21] Appl. No.: 638,874

Related U.S. Application Data

[62] Division of Ser. No. 487,423, July 10, 1974, Pat. No. 3,998,810.

[30] Foreign Application Priority Data

Aug. 3, 1973 Germany .......................... 2339396

[52] U.S. Cl. ............................ 424/247; 424/244; 424/274; 424/330; 260/239 B; 260/243 A; 260/315; 260/570.6
[51] Int. Cl.² ............... A61K 31/54; C07D 279/24
[58] Field of Search ............ 260/243 A, 570.7 OH; 424/247

[56] References Cited

UNITED STATES PATENTS

| | | | |
|---|---|---|---|
| 3,203,992 | 8/1965 | Kunz et al. | 260/570.7 OH |
| 3,275,629 | 9/1966 | Balzer | 260/570.7 OH X |
| 3,888,898 | 6/1975 | Koppe et al. | 260/465 E |

FOREIGN PATENTS OR APPLICATIONS

| | | | |
|---|---|---|---|
| 2,109,651 | 9/1971 | Germany | 260/570.7 OH |
| 2,401,374 | 7/1974 | Germany | 260/570.7 OH |

OTHER PUBLICATIONS

B 487,423, Mar. 1976, Wiedemann et al., 260/239 D.

*Primary Examiner*—John D. Randolph
*Attorney, Agent, or Firm*—Burgess, Dinklage & Sprung

[57] ABSTRACT

New N-substituted 1-amino-3-phenoxy-propan-2-ol compounds of the formula:

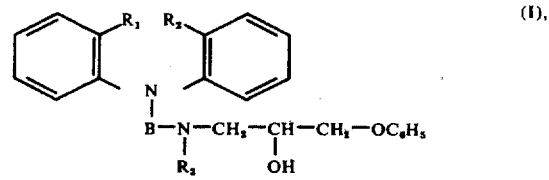

wherein
$R_1$ and $R_2$ are, individually, hydrogen or, taken together, represent a sulfur linkage, an ethylene radical or a valency bond;
B is straight or branched chain alkylene or hydroxyalkylene of from 2 to 5 carbon atoms; and
$R_3$ is hydrogen or alkyl of up to 3 carbon atoms;
and the physiologically compatible salts thereof; possess valuable cardiac and circulatory activity.

12 Claims, No Drawings

N-SUBSTITUTED 1-AMINO-3-PHENOXY-PROPAN-2-OL COMPOUNDS AND THERAPEUTIC COMPOSITIONS CONTAINING THEM

This is a division of application Ser. No. 487,423, filed July 10, 1974 now U.S. Pat. No. 3,998,810 granted Dec. 21, 1976.

The present invention relates to new N-substituted 1-amino-3-phenoxy-propan-2-ol compounds and to thereapeutic compositions containing them.

The new N-substitued 1-amino-3-phenoxy-propan-2-ols according to the present invention are compounds of the formula:

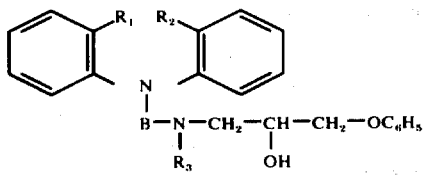

(I), wherein
$R_1$ and $R_2$ are, individually, hydrogen or, taken together, represent a sulfur linkage, an ethylene radical or a valency bond;
B is straight or branched chain alkylene or hydroxyalkylene of from 2 to 5 carbon atoms; and
$R_3$ is hydrogen or alkyl of up to 3 carbon atoms; and the physiologically compatible salts thereof.

We have found that the new compounds of formula (I) possess valuable cardiac and circulatory activities.

The new compounds of formula (I) can be prepared, for example, by one of the following methods:

a. reaction of an amine of the general formula:

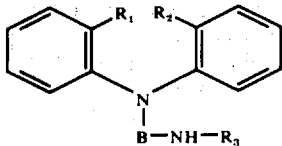

(II), wherein $R_1$, $R_2$, $R_3$ and B have the same meanings as above, with 1,2-epoxy-3-phenoxy-propane or with a reactive derivative thereof; or b. reaction of a compound of the general formula:

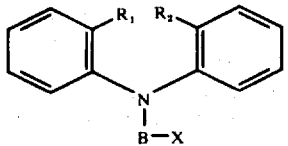

(III), wherein $R_1$, $R_2$ and B have the same meanings as above and X is a reactive group, or, if the compound (I) is to be substituted in the alkylene chain B by a hydroxyl group, B-X can also represent an epoxyalkyl radical, with an amine of the general formula:

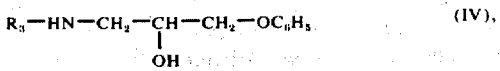

(IV), wherein $R_3$ has the same meaning as above, whereafter, if desired, the compounds obtained are converted into their physiologically compatible salts.

Reactive derivatives of 1,2-epoxy-3-phenoxy-propane which can be used include, for example, the corresponding halohydrins.

As reactive groups X, there can be used, for example, halogen atoms or mesyloxy or tosyloxy radicals.

The reaction according to processes (a) and (b) can be carried out by simple heating of the components but, if desired, the reaction can be carried out in the presence of an inert, high boiling point solvent. If, instead of the epoxides, there are used the corresponding halohydrins, then, for the binding of the hydrohalic acid split off, it is expedient to add a base, for example an excess of the amine used.

The basic products obtained can be converted by means of inorganic or organic acids, in known manner, into the corresponding physiologically compatible salts. Examples of inorganic acids include hydrohalic acids, sulfuric acid and phosphoric acid and examples of organic acids include acetic acid, lactic acid, maleic acid, fumaric acid, tartaric acid and citric acid.

The following Examples illustrate the preparation of the compounds of the invention;

EXAMPLE 1

Preparation of 1-[10,11-dihydrodibenz(b,f)azepinyl(5)-ethylamino]-2-hydroxy-3-phenoxy-propane A mixture of 6.75 g. 10,11-dihydrodibenz(b,f)azepinyl-(5)-ethylamine and 4.67 g. 1,2-epoxy-3-phenoxy-propane was heated for 6 hours at 170° C. The viscous oil obtained was triturated with ether and the solid material thus obtained was recrystallized from isopropanol, with the addition of active charcoal. 3.6 g. (32.7% of theory) of colorless crystals of 1-[10,11-dihydrodibenz(b,f)-azepinyl-(5)-ethylamino]-2-hyroxy-3-phenoxy-propane were obtained; m.p. 98°–100° C.

EXAMPLE 2

Preparation of 1-[10,11-dihydrodibenz(b,f)azepinyl-(5)-isopropylamino]-2-hydroxy-3-phenoxy-propane A mixture of 14.25 g. 1-[10,11-dihydrodibenz(b,f)azepinyl-(5)]-2-aminopropane and 8.87 g. 1,2-epoxy-3-phenoxy-propane was heated for 2 hours at 140° C. by subsequent trituration of the reaction mixture with ether and recrystallization from isopropanol, with the use of active charcoal, there were obtained 4.4 g. (19.4% of theory) of colorless crystals of 1-[10,11-dihydrodibenz(b,f)azepinyl-(5)-isopropylamino]-2-hydroxy-3-phenoxy-propane; m.p. 119°–120° C.

The 1-[10,11-dihydrodibenz(b,f)azepinyl-(5)]-2-aminopropane used as starting material was prepared in the following manner:

111 g. 1-[10,11-dihydrodibenz(b,f)azepinyl-(5)]-2-mesyloxy-propane (prepared from 1-[10,11-dihydrodibenz(b,f)azepinyl-(5)]-2-hydroxypropane and mesyl chloride in pyridine at 5° C., colorless crystals; m.p. 102°–105° C.; yield 53.5% of theory), 230 ml. liquid ammonia and 600 ml. toluene were heated in an autoclave for 5 hours at 110° C. The reaction mixture was then evaporated to dryness, the residue was taken up in water and 2N aqueous sodium hydroxide solution was added thereto until an alkaline reaction was obtained, followed by extraction with methylene chloride. The methylene chloride was then evaporated off and the residue was fractionally distilled under reduced pressure to give 60.8 g. (72% of theory) 1-[10,11-dihydrodibenz(b,f)azepinyl-(5)]-2-aminopropane in the form of a yellowish oil; b.p. 167° C./0.2 mm.Hg.

EXAMPLE 3

Preparation of
1-[3-(10,11-dihydrodibenz(b,f)-azepinyl-(5))-2-hydroxy-propylamino]-2-hydroxy-3-phenoxy-propane A mixture of 6.3 g. 5-(2,3-epoxypropyl)-10,11-dihydrodibenz(b,f)azepine and 4.2 g. 1-amino-3-phenoxypropan-2-ol was heated for 65 minutes at 160° C. The reaction mixture was thereafter triturated with ether and the material thus obtained was recrystallized from ethyl acetate. There were obtained 2.6 g. (25% of theory) of colorless crystals of 1-[3-(10,11-dihydrodibenz(b,f)azepinyl-(5))-2-hydroxypropylamino]-2-hydroxy-3-phenoxy-propane; m.p. 103°–104° C.

EXAMPLE 4

Preparation of
1-[carbazolyl-(9)-ethylamino]-2-hydroxy-3-phenoxypropane 29 g. 9-(2-aminoethyl)-carbazole and 21.5 g. 1,2-epoxy-3-phenoxypropane were heated for 6 hours at 170° C. By triturating the glassy reaction product with ether and recrystallizing it from isopropanol, with the use of active charcoal, there were obtained 13.5 g. (27% of theory) of colorless crystals of 1-[carbazolyl-(9)-ethylamino]-2-hydroxy-3-phenoxy-propane; m.p. 94°–96° C.

In an analogous manner, by the reaction of 9-(2-aminopropyl)-carbazole with 1,2-epoxy-3-phenoxypropane, there was obtained 1-[carbazolyl-(9)-isopropylamino]-2-hydroxy-3-phenoxy-propane in the form of colorless crystals; m.p. 128°–130° C.

The 9-(2-aminopropyl)-carbazole used as starting material was obtained from 9-(2-methane-sulfonyloxypropyl)-carbazole (m.p. 125°–127° C.; obtained from the corresponding carbinol by reaction with mesyl chloride in pyridine at 5° C.) by reaction with liquid ammonia in toluene in an autoclave.

In an analogous manner, the reaction of 9-(3-aminopropyl)-carbazole with 1,2-epoxy-3-phenoxy-propane gave 1-[3-carbazolyl-(9)-propylamino]-2-hydroxy-3-phenoxy-propane in the form of colorless crystals; m.p. 113°–114° C.

EXAMPLE 5

Preparation of
1-[N-(carbazolyl-(9)-ethyl)-methylamino]-2-hydroxy-3-phenoxy-propane A mixture of 6.72 g. 9-(2-methylaminoethyl)-carbazole and 4.73 g. 1,2-epoxy-3-phenoxy-propane was heated for 10 minutes at 160° C. The reaction product was dissolved in 25 ml. ethanol and mixed with 7 g. fumaric acid, whereafter the reaction mixture was boiled under reflux for 5 minutes, cooled and filtered with suction. 13.4 g. (91% of theory) of colorless crystals of 1-[N-(carbazolyl-(9)-ethyl)-methylamino]-2-hydroxy-3-phenoxy-propane were obtained which crystallized with 1 mol fumaric acid; m.p. 150°–151° C.

The 9-(2-methylaminoethyl)-carbazole used as starting material was prepared by the reaction of 9-(2-methanesulfonyloxyethyl)-carbazole (m.p. 143° C.; prepared from the carbazole and mesyl chloride by reaction with pyridine at 5° C.) with methylamine in toluene in an autoclave for 5 hours at 110° C. The product was an oil which boiled at 153°–154° C./0.2 mm.Hg.

EXAMPLE 6

Preparation of
1-[N-(3-carbazolyl-(9)-propylmethylamino]-2-hydroxy-3-phenoxy-propane A mixture of 5.0 g. 9-(3-methylaminopropyl)-carbazole and 3.3 g. 1,2-epoxy-3-phenoxy-propane was heated for 10 minutes at 160° C. by triturating the reaction product with ether, there were obtained 4.9 g. (60% of theory) of colorless crystals of 1-[N-(3-carbazolyl-(9)-propyl)-methylamino]-2-hydroxy-3-phenoxy-propane; m.p. 92°–93° C.

EXAMPLE 7

Preparation of
1-[phenothiazinyl-(10)-isopropylamino]-2-hydroxy-3-phenoxy-propane A mixture of 25.6 g. 10-(2-aminopropyl)-phenothiazine and 15.8 g. 1,2-epoxy-3-phenoxy-propane was heated for 3 hours at 140° C. and for one further hour at 150° C. The crude reaction product was purified over a column of silica gel (elution agent: chloroform-methanol 9:1). From the second fraction, after evaporation, there were obtained 14.1 g. of a brown oil which was heated under reflux for 5 minutes with an excess of fumaric acid in 30 ml. ethanol. The crystals which precipitated out upon cooling were recrystallized twice from methanol, with the addition of active charcoal. There were obtained 12.0 g. (26% of theory) of colorless crystals of 1-[phenothiazinyl-(10)-isopropylamino]-2-hydroxy-3-phenoxy-propane which crystallized with 0.5 mol fumaric acid; m.p. 198°–200° C.

In an analogous manner, by the reaction of 10-(2-aminoethyl)-phenothiazine with 1,2-epoxy-3-phenoxypropane, there was obtained 1[phenothiazinyl-(10)-ethyl-amino]-2-hydroxy-3-phenoxy-propane in the form of colorless crystals; m.p. 73°–75° C.

EXAMPLE 8

Preparation of
1-(2-diphenylaminoethylamino)-2-hydroxy-3-phenoxy-propane

A mixture of 6.4 g. N-(2-aminoethyl)-diphenylamine and 4.7 g. 1,2-epoxy-3-phenoxy-propane was heated for 10 minutes at 160° C. The reaction product was triturated with ether and then recrystallized from isopropanol. 4.7 g. (43% of theory) of colorless crystals of 1-(2-diphenylaminoethylamino)-2-hydroxy-3-phenoxy-propane were obtained; m.p. 95°–96° C.

EXAMPLE 9

Preparation of
1-[3-(10,11-dihydrodibenz(b,f)azepinyl-(5))-propylamino]-2-hydroxy-3-phenoxypropane A mixture of 7.3 g. 5-(3-chloropropyl)-10,11-dihydrodibenz(b,f)azepine, 4.5 g. 3-phenoxy-2-hydroxypropylamine and 7.0 g. N-ethyl-diisopropylamine in 50 ml. dioxan was heated under reflux for 5 hours. The reaction mixture was then evaporated to dryness in a vacuum, the residue was stirred with a copious amount of ether and N-ethyl-diisopropylamine hydrochloride formed was filtered off with suction. By evaporation of the filtrate, there were obtained 9.7 g. (89% of theory) of an oil. Further, purification was carried out over a silica gel column using, as eluant, first chloroform and then chloroform-methanol (9:1). From the fourth fraction, there were obtained, by digestion with ether, colorless crystals of 1-[3-(10,11-dihydrodibenz(b,f)azepinyl-(5))-propyl-amino]-2-hydroxy-3-phenoxy-propane which, after recrystallization from ether, melted at 71°–73° C.

The pharmacological effectiveness of the compounds in accordance with the invention and namely their effectiveness as cardiac and circulatory agents was evaluated by the increase in the heart minute volume. A criterion of the improvement of the blood supply to the organs lies in the increase of the heart minute volume as measured in the aorta of unanesthetized dogs following oral application of an appropriate pharmaceutical.

The tests were carried out on unanesthetized dogs having electromagnetic flowmeters chronically implanted in the aorta ascendens. The mechanical zero line was determined by means of simultaneously chronically implanted sealing flaps or by means of the exact adjustment of an electronic gate of the electro flowmeter. The test compounds were administered to the animal through stomach tubes. All of the compounds were employed dissolved in 10 ml distilled water to which 5% "Lutrol 9" (polyethylene oxide molecular weight - 400) had been added.

The initial test dosages employed were not necessarily uniform, as in some instances, lower doses were first used and it was further determined whether higher doses would possibly be more effective.

The following compounds were employed in the test procedure:

A.         1-[10,11-dihydrodibenz(b,f)azepinyl-(5)-ethylamino]-2-hydroxy-3-phenoxy-propane
B.        1-[10,11-dihydrodibenz(b,f)azepinyl-(5)-isopropylamino]-2-hydroxy-3-phenoxy-propane
C.       1-[3-(10,11-dihydrodibenz(b,f)azepinyl-(5))-2-hydroxy-propylamino]-2-hydroxy-3-phenoxy-propane
D.       1-[3-carbazolyl-(9)-propylamino]-2-hydroxy-3-phenoxy-propane
E.       1-[N-(3-carbazolyl-(9)-propyl)-methylamino]-2-hydroxy-3-phenoxy-propane
F.         1-[phenothiazinyl-(10)-isopropyl-amino]-2-hydroxy-3-phenoxy-propane
G.      1-[phenothiazinyl-(10)-ethylamino]-2-hydroxy-3-phenoxy-propane
H.       1-(2-diphenylaminoethylamino)-2-hydroxy-3-phenoxy-propane
I. COMPLAMIN {xantinolnicotinate = 7-[2-hydroxy-3-(N-methyl-$\beta$-hydroxyethylamino)-propyl]-theopylline}

The compounds in accordance with the invention exhibit, i.e., are possessed of special cardiac and circulatory activities and specifically of circulation stimulating activites. As there are no known structurally similar compounds possessed of these properties, in the test procedures, the known compound (COMPLAMIN), xantinolnicotinate = 7-[2-hydroxy-3-(N-methyl-$\beta$-hydroxyethylamino)-propyl]-theophylline (Compound I) was employed as a comparison compound.

The results were as follows:

TABLE

INCREASE IN THE BLOOD TIME VOLUME IN THE AORTA OF UNANESTHETIZED DOGS

| COMPOUND | DOSAGE MG/KG ORAL | MAX. INCREASE OF BLOOD TIME VOLUME IN % AS COMPARED TO THE CONTROL (= 100%) |
|---|---|---|
| I | 25 | 110 |
| A | 0.5 | 129 |
| B | 0.5 | 190 |
| C | 0.5 | 180 |
| D | 0.5 | 140 |
| E | 0.5 | 140 |
| F | 0.5 | 167 |
| G | 0.5 | 133 |
| H | 0.5 | 115 |

RESULTS:

It can be seen from the preceding Table that 25.0 mg/kg xantinolnicotinate (oral) produced an increase in the heart minute volume of from 100 to 110%. The result was reproducible in each instance so that it can be taken as the comparison value. The novel compounds of the invention were administered in a dosage of 0.5 mg/kg, that means that this dose of xantinolnicotinate was 50 fold of the dose of the new compounds. This consequently establishes for the compounds of the invention a marked superiority with respect to effect produced i.e., increase in heart minute volume in relation to xantinolnicotinate and this was true for every compound tested.

Thus, it can be seen that the compounds of the invention administered in low dosages (0.5 mg/kg, oral) produce in the unanesthetized dog an increase in the peripheral blood circulation of the organs by an emptying of the venous blood storage depots, i.e., through an increase of the heart minute volume.

As indicated hereinbefore, the compounds of the present invention are useful for the treatment of conditions associated with cardiac and impaired circulatory phenomena and for this purpose the active compounds are associated with a pharmaceutically acceptable carrier in a form suitable for administration both perorally or parenterally.

The dosage of the novel compounds of the present invention for the treatment of the conditions as set out above, depends on the age, weight and condition of the patient being treated. Generally speaking, for adult oral administration, the preferred unit dosage is 1 mg — 50 mg of active compound with a suitable pharmaceutical diluent and/or lubricant.

The new compounds according to the present invention can be administered enterally or parenterally in admixture with solid or liquid pharmaceutical diluents or carriers. As injection medium, it is preferred to use water which contains the conventional additives for injection solutions, for example stabilizing agents, solubilizing agents or buffers. Additives of this kind include, for example, tartrate and citrate buffers, ethanol, complex-forming agents, such as ethylenediaminetetraacetic acid and the non-toxic salts thereof, and high molecular weight polymers, such as liquid polyethylene oxide, for viscosity regulation. Solid carrier materials include, for example, starch, lactose, mannitol, methyl-cellulose, talc, highly dispersed silicic acids, high molecular weight fatty acids, such as stearic acid, gelatine, agar-agar, calcium phosphate, magnesium stearate, animal and vegetable fats and solid high molecular weight polymers, such as polyethylene glycols. Compositions suitable for oral administration can, if desired, contain flavoring and/or sweetening materials.

It will be understood that the specification and examples are illustrative but not limitative of the present invention and that other embodiments within the spirit and scope of the invention will suggest themselves to those skilled in the art.

What is claimed is:

1. N-substituted 1-amino-3-phenoxy-propan-2-ol compound of the formula:

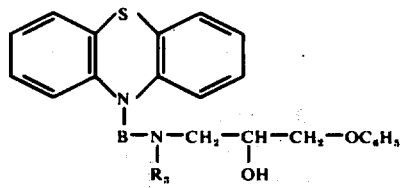

(I).

wherein
R₁ and R₂ are, individually, hydrogen or
R₁ and R₂ taken together represent a sulfur linkage or a valency bond;
B is straight or branched chain alkylene or hydroxyalkylene of from 2 to 5 carbon atoms; and
R₃ is hydrogen or alkyl of up to 3 carbon atoms;
and the physiologically compatible salts thereof.

2. N-substituted 1-amino-3-phenoxy-propan-2-ol compound as claimed in claim 1 wherein B is alkylene of from 2 to 5 carbon atoms.

3. N-substituted 1-amino-3-phenoxy-propan-2-ol compound as claimed in claim 1 wherein B is hydroxyalkylene of from 2 to 5 carbon atoms.

4. N-substituted 1-amino-3-phenoxy-propan-2-ol compound as claimed in claim 1 wherein R₃ is hydrogen.

5. N-substituted 1-amino-3-phenoxy-propan-2-ol compound as claimed in claim 1 wherein R₃ is alkyl of up to 3 carbon atoms.

6. N-substituted 1-amino-3-phenoxy-propan-2-ol compound as claimed in claim 1 designated 1-[phenothiazinyl-(10)-ethylamino]-2-hydroxy-3-phenoxy-propane.

7. N-substituted 1-amino-3-phenoxy-propan-2-ol compound as claimed in claim 1 designated 1-[phenothiazinyl-(10)-isopropylamino]-2-hydroxy-3-phenoxy-propane.

8. Therapeutic composition having cardiac and circulatory activity comprising a pharmaceutically acceptable carrier and, in effective amounts, an N-substituted 1-amino-3-phenoxy-propan-2-ol compound as claimed in claim 1.

9. Method of treating a subject with cardiac or circulatory impairments which method comprises administering to such subject an effective amount of an N-substituted 1-amino-3-phenoxy-propan-2-ol compound of the formula:

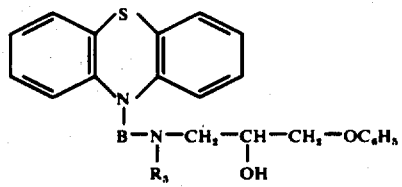

(I).

wherein
R₁ and R₂ are, individually, hydrogen or
R₁ and R₂ taken together represent a sulfur linkage, an ethylene radical or a valency bond;
B is straight or branched chain alkylene or hydroxyalkylene of from 2 to 5 carbon atoms; and
R₃ is hydrogen or alkyl of up to 3 carbon atoms;
and the physiologically compatible salts thereof.

10. Method as claimed in claim 9 wherein said compound is at least one of:
1-[phenothiazinyl-(10)-ethylamino]-2-hydroxy-3-phenoxy-propane; and
1-[phenothiazinyl-(10)-isopropylamino]-2-hydroxy-3-phenoxy-propane.

11. Method as claimed in claim 9 wherein said compound is applied at a dosage of 0.1 to 5 mg/kg of said compound.

12. Method as claimed in claim 9 wherein said compound is applied in unit dosage form wherein each unit dosage contains 1 mg to 50 mg of active compound.

* * * * *